(12) United States Patent
Crawford

(10) Patent No.: US 8,678,995 B2
(45) Date of Patent: Mar. 25, 2014

(54) PELVIC IMPLANT AND DELIVERY SYSTEM

(75) Inventor: Scott Crawford, Phoenix, AZ (US)

(73) Assignee: AMS Research Corporation, Minnetonka, MN (US)

( * ) Notice: Subject to any disclaimer, the term of this patent is extended or adjusted under 35 U.S.C. 154(b) by 467 days.

(21) Appl. No.: 13/057,186

(22) PCT Filed: Aug. 5, 2009

(86) PCT No.: PCT/US2009/052843
§ 371 (c)(1),
(2), (4) Date: Feb. 2, 2011

(87) PCT Pub. No.: WO2010/017291
PCT Pub. Date: Feb. 11, 2010

(65) Prior Publication Data
US 2011/0160529 A1    Jun. 30, 2011

Related U.S. Application Data

(60) Provisional application No. 61/086,201, filed on Aug. 5, 2008.

(51) Int. Cl.
*A61F 2/00* (2006.01)
(52) U.S. Cl.
USPC .......................................... 600/37

(58) Field of Classification Search
USPC ................. 600/29, 30, 37, 562, 564, 570
See application file for complete search history.

(56) References Cited

U.S. PATENT DOCUMENTS

| 5,643,288 A | 7/1997 | Thompson |
| 5,807,403 A * | 9/1998 | Beyar et al. .................. 606/232 |
| 2002/0147382 A1 * | 10/2002 | Neisz et al. ..................... 600/29 |

FOREIGN PATENT DOCUMENTS

| WO | WO 2004017845 A1 * | 3/2004 |
| WO | WO 2004/017845 | 4/2004 |
| WO | WO 2007/097994 | 8/2007 |
| WO | WO 2008/057261 | 5/2008 |

* cited by examiner

*Primary Examiner* — Christine Matthews
*Assistant Examiner* — Joshua D Lannu
(74) *Attorney, Agent, or Firm* — Kagan Binder, PLLC

(57) ABSTRACT

Described and depicted are pelvic sling implant and delivery systems. The sling implants can be used in treating stress incontinence and other pelvic floor disorders. The sling systems can include a mesh extension or support portion and one or more tip anchors. A delivery tool can include a handle (61), a needle (62) and a sheath (70), with the sheath having an elongate shaft portion slidable along at least a portion of the needle. The sheath can further include a distal hood portion having opposed flared portions (78) defining interior pleat channels adapted to selectively seat tine ends of the anchors.

22 Claims, 6 Drawing Sheets

PELVIC IMPLANT AND DELIVERY SYSTEM

RELATED APPLICATIONS

This application claims benefit from International Application No. PCT/US2009/052843, which was filed Aug. 5, 2009, which in turn claims priority to and the benefit of U.S. Provisional Application Ser. No. 61/086,201, filed Aug. 5, 2008, with the above-identified applications and disclosures being incorporated herein by reference in their entireties.

FIELD OF THE INVENTION

The invention relates to apparatus and methods for treating pelvic conditions by use of a pelvic implant to support pelvic tissue and, more particularly, to a surgical pelvic implant and delivery system for securing and deploying the pelvic implant.

BACKGROUND OF THE INVENTION

Pelvic health for men and women is a medical area of increasing importance, at least in part due to an aging population. Examples of common pelvic ailments include incontinence (fecal and urinary) and pelvic tissue prolapse (e.g., female vaginal prolapse). Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female SUI occurs when the patient is physically stressed.

One cause of urinary incontinence is damage to the urethral sphincter. Other causes include the loss of support of the urethral sphincter, such as can occur in males after prostatectomy or following radiation treatment, or that can occur due to pelvic accidents and aging related deterioration of muscle and connective tissue supporting the urethra. Other causes of male incontinence include bladder instability, over-flowing incontinence, and fistulas.

The female's natural support system for the urethra is a hammock-like supportive layer composed of endopelvic fascia, the anterior vaginal wall, and the arcus tendineus. Weakening and elongation of the pubourethral ligaments and the arcus tendineus fascia pelvis, and weakening of the endopelvic fascia and pubourethral prolapse of the anterior vaginal wall, may have a role in the loss of pelvic support for the urethra and a low non-anatomic position that leads to urinary incontinence.

In general, urinary continence is considered to be a function of urethral support and coaptation. For coaptation to successfully prevent or cure incontinence, the urethra must be supported and stabilized in its normal anatomic position. A number of surgical procedures and implantable medical devices have been developed over the years to provide urethral support and restore coaptation.

Another known implant system includes the use of a sling device having a self-fixating anchor tip at a distal end of one or more extension portions. An example of such a sling device is sold by American Medical Systems of Minnetonka, Minn. as the MiniArc® single incision sling system. The self-fixating tip can be placed at and secured within internal tissue of the pelvic region to support the implant end extension and pelvic tissue that is supported by the implant. As an example, a self-fixating tip can be placed at tissue of the obturator foramen (this phrase referring to tissue that lies within or spans the obturator foramen, for example the obturator internus muscle, the obturator membrane, or the obturator externus muscle). Other tissue of the pelvic region can also be locations useful for implanting a self-fixating tip. The self-fixating tips can be designed to engage a distal end of an insertion tool to allow the insertion tool to place the self-fixating tip at a desired tissue location by pushing.

Embodiments of these self-fixating tips can be designed to provide desired function and performance in positioning and tissue attachment. For example, a self-fixating tip can be designed to provide desirably low input force, desirably high pullout force, and reduced trauma caused by passage of the self-fixating tip or an associated insertion tool. Varying functional goals can be achieved by selecting various size and shape features for the self-fixating tip, such as relatively reduced overall dimensions (length or diameter) of the tip; and size, shape, and number of lateral extensions. Further, this self-fixating tip system reduces trauma based on the ability to avoid tissue passages next to critical structure; and reduced trauma due to the ability to eliminate the need for local stab (external) incisions otherwise required for needle entry and exit sites. While the design is a significant improvement over previous sling and fixation configurations, the positional attachment of the device to the corresponding tissue is limited to the self-fixating tip.

SUMMARY OF THE INVENTION

The present patent application describes pelvic implant and delivery systems and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, vault prolapse, etc.), among others. Embodiments of the implants can include one or more extension support portions, and one or more anchors generally attached to or integrated with the extension portion. The extension portion is generally constructed of a mesh material. The one or more anchors can be provided proximate the ends of the mesh extension portion to increase fixation until tissue in-growth occurs. The anchors can be fixating tips placed at and securable within internal tissue of the pelvic region to further assist in supporting the implant device. The anchors can be configured of various sizes and shapes. The anchors of the implant can be adapted to engage a distal end of an insertion tool to allow the insertion tool to place the anchors at a desired tissue location by pushing the anchor into the fibrous tissue.

The insertion or introducer delivery tool can include a thin elongate needle that attaches to a handle at a proximal end of the needle, with a distal end of the needle adapted to engage the anchors. The needle can be generally straight to facilitate deployment of the implant.

In one embodiment, the delivery tool can include a sheath adapted to extend along and at least partially surround or shroud the needle. The sheath can include an elongate portion and a hood. The elongate portion includes a lumen or channel therethrough to slidably receive at least a portion of the needle. The hood can further include distinct flaring portions (e.g., generally arcuate or contoured) configured to create a spatial opening between the flaring portions. A region of the flaring portions defines inner-facing or interior pleat openings or channels adapted to receive and retain respective ends of the anchor tines.

In one embodiment, the invention contemplates a method of treating urinary incontinence in male and female patients (e.g., SUI) in a minimally invasive manner including injecting a local anesthetic; creating one medial (e.g., transvaginal) incision under the mid-urethra; inserting a urinary incontinence sling through the one transvaginal incision, anchoring the urinary incontinence sling, and closing the incision.

Another aspect of the invention includes a combination (e.g., kit, system, etc.) of a sling implant, as described herein, including one or more anchors. The kit also includes one or more insertion tools or systems useful in securely deploying, positioning and anchoring the sling.

BRIEF DESCRIPTION OF THE DRAWINGS

Other features and advantages of the present invention will be seen as the following description of particular embodiments progresses in conjunction with the drawings.

DETAILED DESCRIPTION OF THE INVENTION

Figure 1:
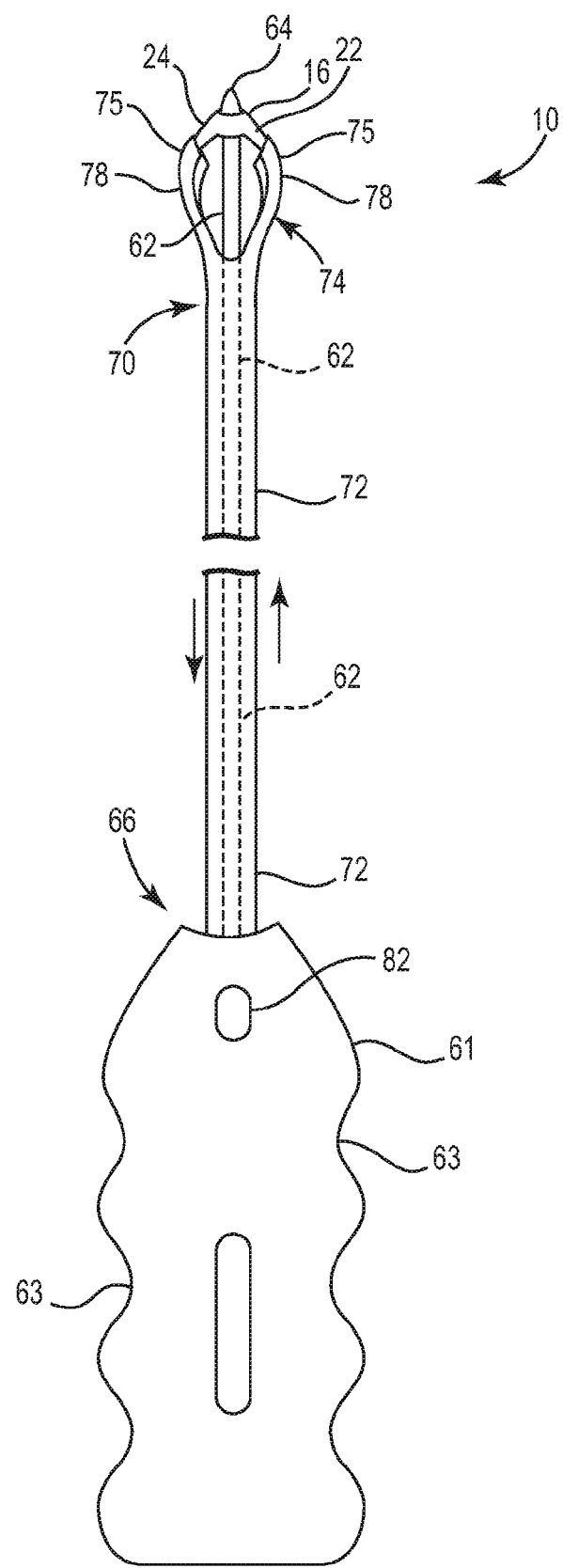
FIG. 1 is a side schematic view of a sling implant and delivery system in accordance with an embodiment of the present invention.

The following description is meant to be illustrative and not limiting. Other embodiments of this invention will be apparent to those of ordinary skill in the art in view of this description and corresponding figures.

The present invention is directed to surgical instruments, assemblies, and implantable articles for treating pelvic floor disorders such as fecal or urinary incontinence, including SUI, prolapse, etc. According to various embodiments, a surgical sling implant can be used to treat a pelvic condition, including the specific examples of implanting a support implant to treat a condition such as vaginal vault prolapse or incontinence (male or female). An implant can be positioned in a male or a female to treat disorders such as urge incontinence, mixed incontinence, overflow incontinence, functional incontinence, fecal incontinence, or for female conditions including prolapse (e.g., vaginal or uterine), enteroceles (e.g., of the uterus), rectoceles, cystocele, and anatomic hypermobility.

The sling implant or system may include portions or sections that are synthetic or constructed of biological material (e.g., porcine, cadaveric, etc.). Extension support portions may be constructed of a synthetic mesh such as a polypropylene, or other compatible materials. Examples of implant products that may be useful according to the present description, include those sold commercially by American Medical Systems, Inc., of Minnetonka Minn., under the trade name MiniArc® for treating urinary incontinence. PCT Patent Publication Nos. 2008/057261 and 2007/097994 disclose various pelvic implant structures, procedures, systems and methods or techniques capable of use with the present invention and are, therefore, incorporated fully herein by reference.

In one embodiment of the present invention, as shown in FIGS. 1-8, an incontinence sling system 10 can be installed to help maintain continence by supporting the urethra during times of increased abdominal pressure. Delivery devices and tools are used to deploy, position and anchor a sling implant 12. The sling 12 can be implanted through a single incision in the vaginal wall for females, or perineal floor for males, and attached to (e.g., anchored to) the obturator internus muscle on either side of the urethra. Only requiring one incision in the vaginal wall (for females) or perineum (for males) eliminates additional incisions such as external incisions used in some methods of implanting urethral slings. The sling 12 and its methods of implantation are, therefore, a reduced or "minimally" invasive treatment option for patients suffering from urinary incontinence. In alternate embodiments, sling 12 may be anchored at other locations besides the obturator internus muscle, such as, for example, the obturator membrane or the obturator externus muscle. One method may be to implant the sling 12 having end tips at opposing extension portions, without penetrating the obturator membrane.

Referring generally to FIGS. 1-5, the sling implant 12 can include an extension portion 14 and one or more end anchors 16. Further, a delivery tool can be included with the system 10 for engaging, positioning, anchoring and disengaging the sling 12 or anchors 16 during use. The sling extension portion 14 can be constructed of a polypropylene mesh material, or other materials known for use with incontinence sling devices. The mesh sling 12 may be woven, knitted, sprayed, or punched from a blank. In one aspect of the invention, mesh sling 12 may include one or more woven, knitted, or interlinked filaments or fibers that form multiple fiber junctions. The fiber junctions may be formed via weaving, knitting, braiding, or through other techniques, including combinations thereof. In addition, the size of the resultant openings or pores of the mesh may be sufficient to allow tissue in-growth and fixation within surrounding tissue. Further, the sling 12 can include one or more band or tracking portions. The band portion, for example, can be a plasma-treated print area of the sling mesh 12 or a separately coupled or integrated band. The band portion facilitates tracking of components of the system 10 during the surgical implant procedure.

Figure 4:
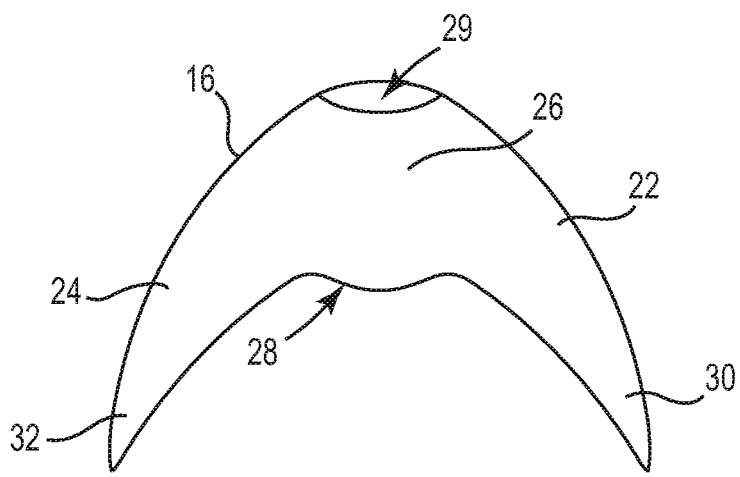
FIG. 4 is a side view of an anchor device in accordance with an embodiment of the present invention.
Figure 5:
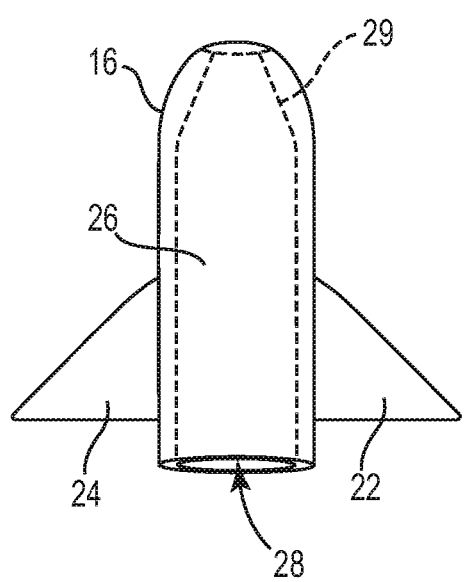
FIG. 5 is a side view of an anchor device in accordance with an embodiment of the present invention.

The extension support portion 14 generally extends between and is coupled or otherwise integrated with two end anchor tips 16. The anchors 16 can include a first anchoring tine or barb 22, a second anchoring tine or barb 24, an intermediate portion 26, and a coupling portion 28, as shown in FIGS. 4-5. Further, the anchoring tines 22, 24 can include respective distal ends 30, 32. While exemplary embodiments of the anchors 16 are depicted in FIGS. 4-5, the shape, size and configuration of the tines 22, 24, distal ends 30, 32, coupling portion 28 and intermediate portion 26 can vary greatly depending on the particular anchoring and deployment requirements. For instance, embodiments of the tines 22, 24 and ends 30, 32 can assume various angled, rounded, arcuate, linear, or other desirable shapes. Embodiments of the anchors 16 can be defined with relatively steep or angled tines 22, 24 (FIG. 4), or with relatively lateral tines 22, 24 (FIG. 5)

The sling extension portion and anchors can exhibit desirable or inherent "adjustability" or "positionability" features, or the system 10 can include a length-adjusting mechanism. Each respective anchoring structure of the sling implant device can be placed within a pelvic tissue such as tissue of the obturator foramen, with properties of the tips and anchors (e.g., dimensions, pullback force, number of lateral extensions, etc.) and sling implant (dimensions such as length between the tips and corresponding anchors) being sufficient to allow placement at the target tissue on one or both sides of the pelvic region. The sling extension portion of the implant can support the urethra, bladder neck, vaginal tissue, etc. Desired positioning of the sling implant, the approximation to the supported tissue (e.g., urethra), or the amount of supportive force placed on the supported tissue can be achieved by selecting desirable placement of the tips and anchors.

An introducer insertion delivery tool 60 can be used to install the sling implant 12. Various types of insertion tools are known, and these types of tools and modifications thereof can be used according to this description to deploy, position and implant the sling and anchors. Examples of useful tools include those described and depicted in incorporated PCT Patent Publication Nos. 2008/057261 and 2007/097994.

Figure 2:
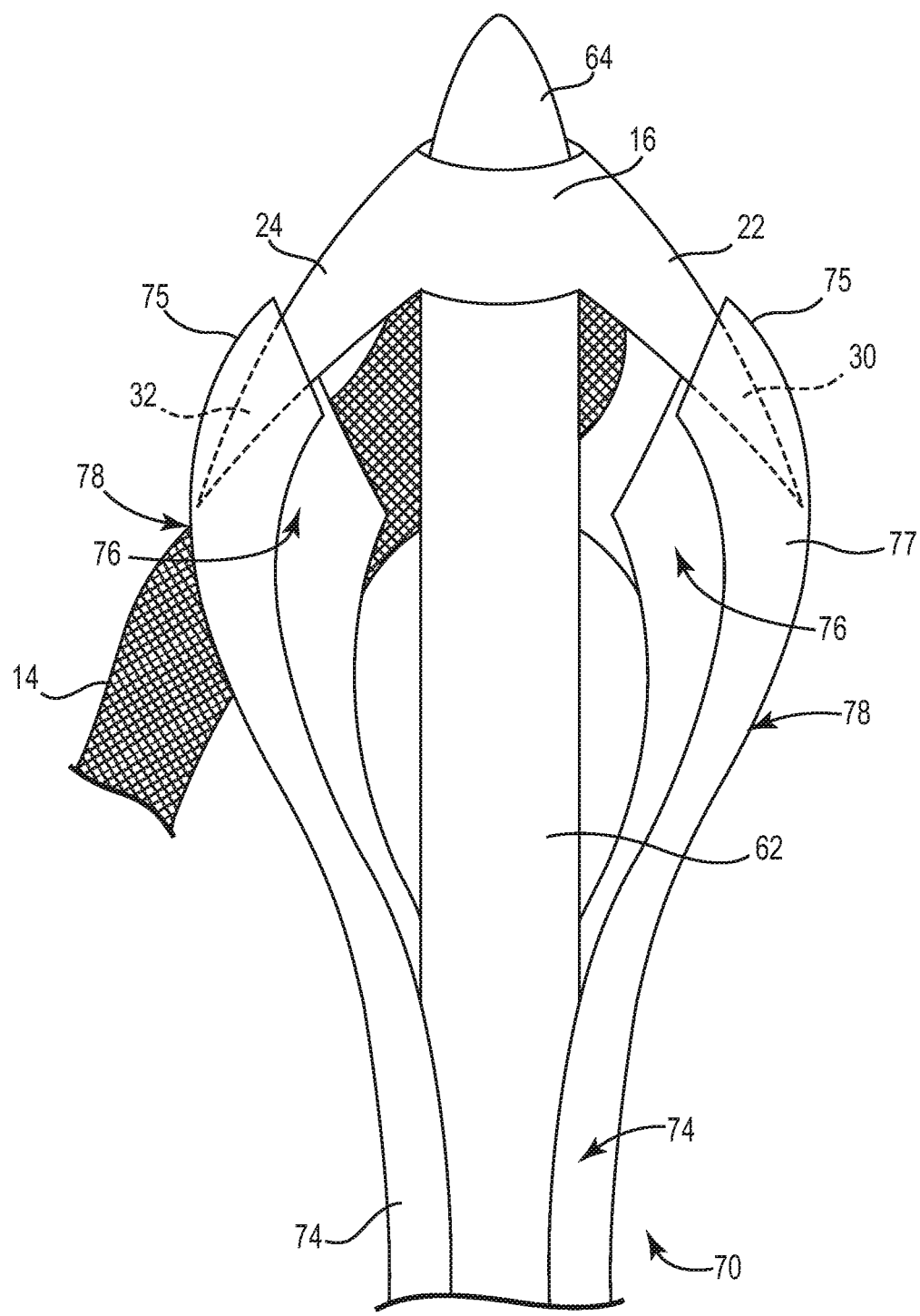
FIG. 2 is a partial view of a sheath hood, needle, anchor and sling implant of the system in accordance with an embodiment of the present invention.
Figure 3:
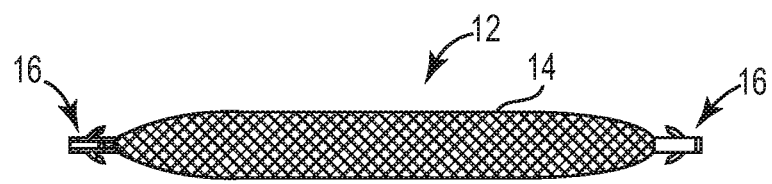
FIG. 3 is a top schematic view of a mesh sling implant in accordance with an embodiment of the present invention.

In one embodiment, as shown in FIGS. 1-2, the insertion tool can include a thin elongate needle 62 that attaches to a handle 61 at a proximal end of the needle 62, with a distal end 64 of the needle adapted to engage an anchor 16. The needle 62 can be generally straight, or curved in alternative embodiments. The needle 62 can be pushed with the sling system 10 through a tissue passage to insert the sling implant 12 and corresponding anchors 16 within the pelvic region. The needle 62 may be a biocompatible, straight needle portion 62, made of stainless steel, titanium, Nitinol, polymers, plastics, or other individual or combinations of materials. The handle 61 can include gripping portions 63 to facilitate handling by an end user. The introducer 60 should have sufficient structural integrity to position the anchors as desired.

Further, the needle 62 of the tool 60 may mate with or engage the anchor 16 by any manner, including fitting within an internal channel 29 of a body or base of the anchor 16, by fitting with an external portion of a body or base of the anchor 16, or through other attachment techniques or mechanisms known to one of ordinary skill in the art. The coupling portion 28, or other portions of the anchor 16, can be adapted for fixation with the extension portion 14 of the sling 12. The anchor 16 can engage with the distal or end portion 64 of the needle 62 by selective mateable engagement, attachment mechanisms or devices, or other known techniques. The overall dimensions and shapes of the components and structures of the sling system 10 can vary without deviating from the spirit and scope of the present invention. The anchors 16 provide significant holding force to prevent migration during initial tissue fixation and ingrowth.

In one embodiment, the introducer 60 can include a sheath 70 adapted to extend along and at least partially surround or shroud the needle 62, as shown in FIGS. 1-2. The sheath 70 can include an elongate portion 72 and a hood 74. The elongate portion 72 includes a lumen or channel therethrough to slidably receive at least a portion of the needle 62. A proximal end of the elongate portion 72 is disposed with or otherwise attached to the handle 61, and the distal end includes the hood 74. The hood 74 can further include distinct flaring portions 78 (e.g., generally arcuate or contoured) configured to create a spatial opening between the flaring portions 78. A region of the flaring portions 78 can be generally U-shaped or V-shaped to define inner-facing pleat openings or channels 76 adapted to receive and retain respective ends 30, 32 of the anchor tines 22, 24. The hood 74 and flaring portions 78 can serve to cover and protect the ends 30, 32 during deployment of the sling 12. The needle 62 is extendable between the flaring portions 78 and the confronting channels 76 for engagement with a seated anchor 16.

The sheath 70 can be constructed so that portions of the sheath 70 exhibit varying levels of rigidity. In general, the elongate portion 72 can be constructed of a relatively rigid, or semi-rigid, polymer to avoid undesirable buckling during use. Further, a distal portion 75 of the hood flaring portions 78 proximate the channels 76 and adapted to seat the tine ends 30, 32 can be constructed of a relatively soft or flexible polymer material, while a remaining lower portion 77 can be constructed of a more rigid polymer material. Other known and compatible materials can be employed to construct various regions of sheath 70 without deviating from the spirit and scope of the present invention.

The channels 76 can vary in shape and size, depending on the configuration and design of the respective flaring portions 78, and the shape and seating requirements of the receivable anchors 16 during use and deployment of the sling 12.

The handle 61 can include one or more actuators 80 adapted to slidably displace (e.g., retract and extend) the sheath 70 longitudinally along the needle 62. Various known roll wheel, ratchet, slide bar and other actuator mechanisms can comprise the actuator 80. Further, a locking mechanism 82 can be included to selectively stabilize and hold the sheath 70 in place.

Figure 6:
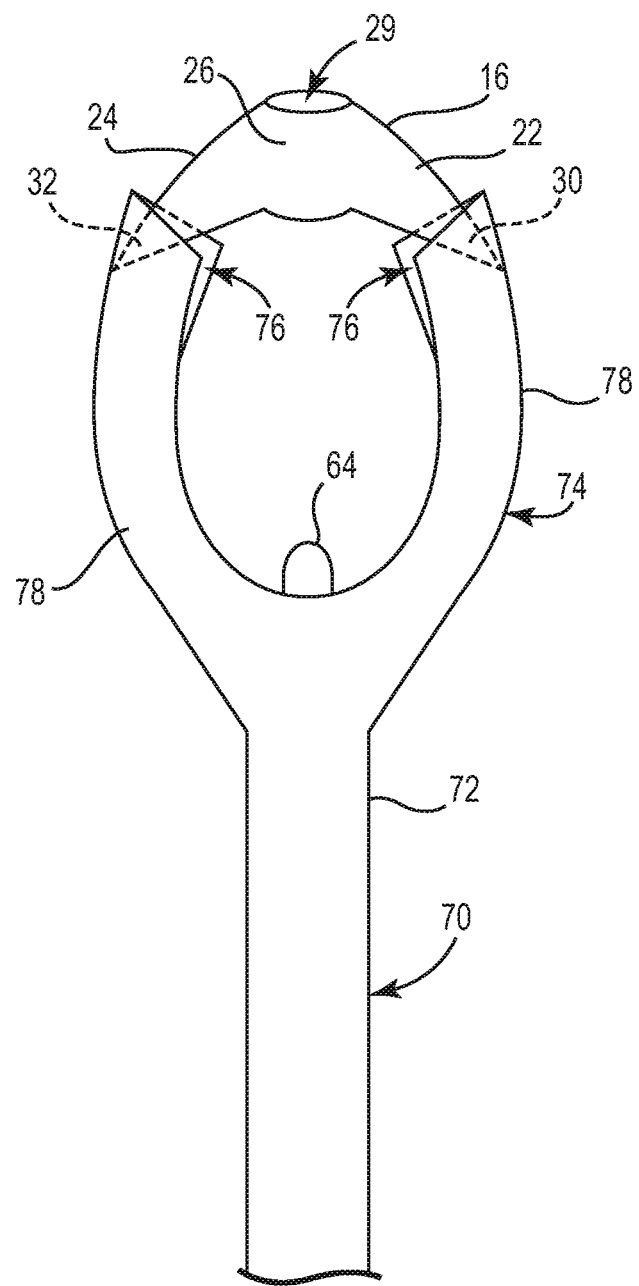
FIG. 6 is a partial schematic view of an anchor seated or docked with the hood of a delivery tool sheath in accordance with an embodiment of the present invention.
Figure 7:
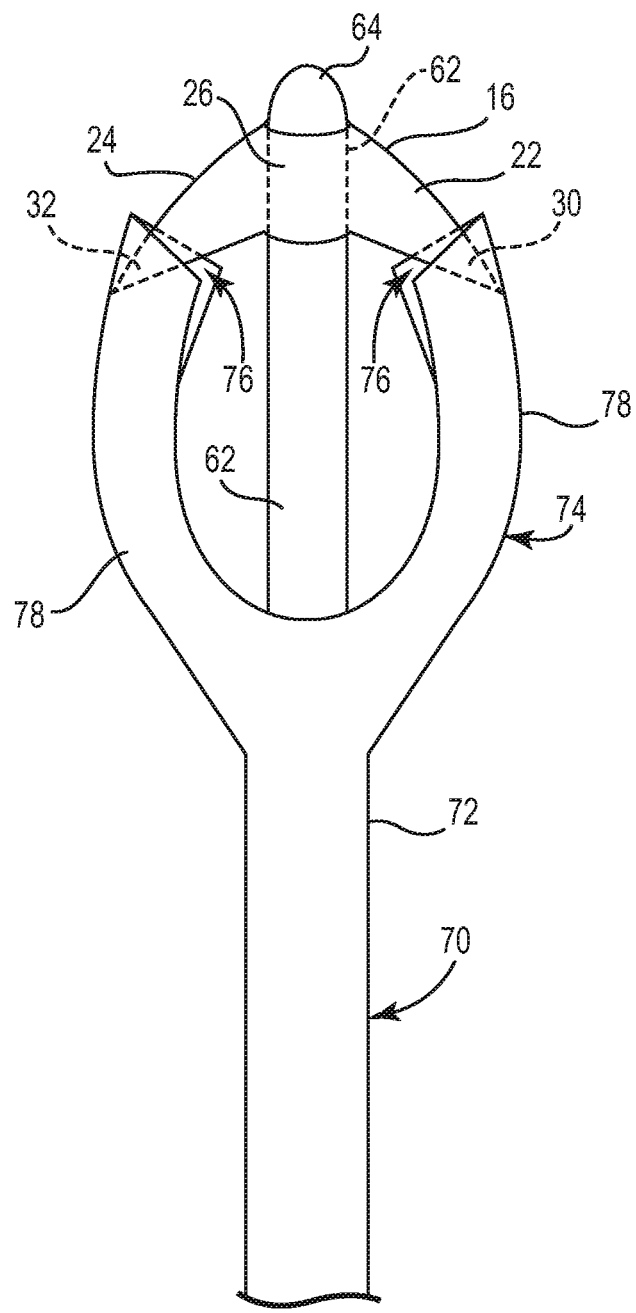
FIG. 7 is a partial schematic view of an anchor seated or docked with the hood of a delivery tool sheath, and a needle engaged with the anchor, in accordance with an embodiment of the present invention.
Figure 8:
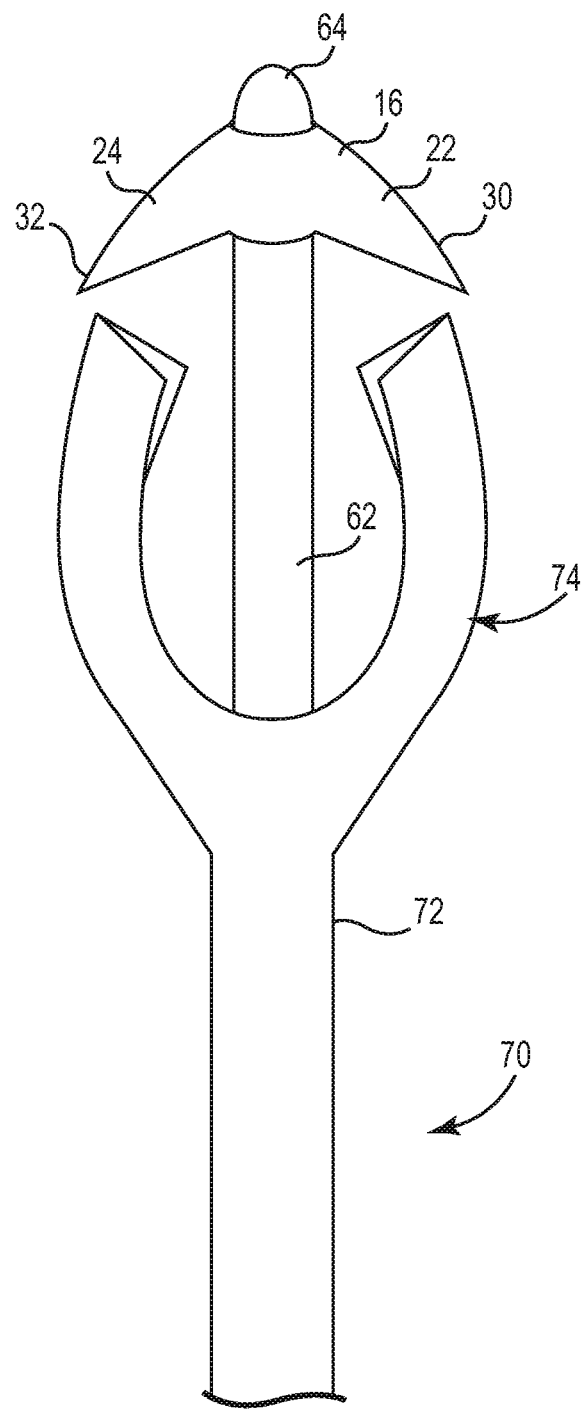
FIG. 8 is a partial schematic view of an anchor unseated or undocked with the hood of a delivery tool sheath, and a needle engaged with the anchor, in accordance with an embodiment of the present invention.

In one aspect of the invention, as shown in FIGS. 6-8, the ends 30, 32 of the anchor 16 are seated or docked within respective pleat channels 76 by advancing the hood 74 up into contact with the anchor 16. The anchor 16 could also be independently or separately seated within the hood 74 without traversal of the sheath 70. With the anchor 16 seated in the hood 74, the sheath 70 can be retracted to engage the distal end 64 of the needle 62 with the anchor 16. As detailed herein, one form of engagement provides an internal channel 29 within the anchor 16 configured to receive and attach to the needle 62. Upon deployment of the sling 12 to the target tissue site within the patient, the anchor 16 can be implanted into the tissue. In one embodiment, the sheath 70 can be slidably retracted to disengage or undock the anchor 16 from the hood 74 to expose the tines 22, 24 for implantation within the tissue. This process can be repeated to deploy, position and implant another anchor 16 of the sling 12 at a different target tissue site. Various steps, and sequential combinations thereof, for docking and deploying the anchor 16 from the sheath 70 and needle 62 are envisioned for implementation with the present invention.

One example of a method according to the invention is a method of treating urinary incontinence by surgical implantation of a urethral sling (e.g., a single, integral, optionally uniform, woven polymeric mesh, with two anchor tips, through a vaginal (for female anatomy) or perineal (for male anatomy) incision, along a tissue path that extends from a region of the urethra to the obturator foramen. These methods can advantageously involve only a single incision (a vaginal incision in a female or a perineal incision in a male) and can exclude the need for any additional incision. The elongate urethral sling 12 is attached at tissue of the opposing obturator foramen by the anchors 16, with the sling extension portion 14 passing below the urethra to support the urethra.

All patents and publications referenced herein, and those patents and publications referenced therein, are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical surgical procedures that are not disclosed and are not necessary to the practice of the present invention.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A pelvic implant delivery system, comprising:
   a handle;
   a needle having a proximal end connected to the handle; and
   a sheath shrouding at least a portion of the needle, the sheath having:
      an elongate shaft portion and a distal hood portion, with the distal hood portion having opposed flared portions defining interior pleat channels adapted to selectively seat tine ends of a pelvic implant anchor device,
   wherein the sheath is slidably movable along at least a portion of the needle and relative to the handle, the handle being stationary relative to the needle.

2. The system of claim 1, wherein the handle includes at least one actuator mechanism to slidably move the sheath along the needle.

3. The system of claim 1, wherein the handle includes a locking mechanism to selectively lock the sheath in place.

4. The system of claim 1, wherein a distal region of each of the opposed flared portions is constructed of a generally flexible material.

5. The system of claim 1, wherein a proximal region of each of the opposed flared portions is constructed of a generally rigid material.

6. The system of claim 1, wherein the opposed flared portions are contoured to define an interior space therebetween.

7. The system of claim 1, further including a sling mesh attached to the pelvic implant anchor device.

8. The system of claim 1, wherein the sheath exhibits varying levels of rigidity.

9. A pelvic implant and delivery system, comprising:
   an implant having a tissue support portion, an extension portion, and an anchor device having tine ends, the anchor device being fixedly secured at an end of the extension portion; and
   a delivery tool, including;
      a handle;
      a needle having a proximal end connected to the handle; and
      a sheath having an elongate shaft portion shrouding and slidable along at least a portion of the needle, and a distal hood portion having opposed flared portions defining interior pleat channels adapted to selectively seat the tine ends of the anchor device.

10. The system of claim 9, wherein the handle includes at least one actuator mechanism to slidably move the sheath along the needle and relative to the handle.

11. The system of claim 9, wherein the handle includes a locking mechanism to selectively lock the sheath in place.

12. The system of claim 9, wherein a distal region of each of the opposed flared portions is constructed of generally flexible polymer material.

13. The system of claim 9, wherein a proximal region of each of the opposed flared portions is constructed of a generally rigid polymer material.

14. The system of claim 9, wherein the opposed flared portions are contoured to define an interior space therebetween.

15. The system of claim 9, wherein a distal end of the needle is adapted to selectively engage the anchor devices.

16. The system of claim 9, wherein the tine ends of the anchor devices are angled downward to facilitate seating within the pleat channels.

17. The system of claim 9, wherein the sheath exhibits varying levels of rigidity.

18. The system of claim 9, wherein the sheath is slidably movable along at least a portion of the needle and relative to the handle, the handle being stationary relative to the needle.

19. A method of treating a pelvic condition, the method comprising:
   creating one incision, the incision being located under the midurethra through the vagina or through a perineal floor;
   providing an implant having a tissue support portion and first and second anchor devices with tine ends, the first and second anchor device being fixedly secured to the tissue support portion;
   providing a delivery tool having a handle, a needle and a sheath, with the sheath having an elongate shaft portion slidable along at least a portion of the needle, and the sheath further having a distal hood portion having opposed flared portions defining interior pleat channels adapted to selectively seat the tine ends of the first and second anchor devices;
   inserting the first anchor device with the delivery tool through the incision and anchoring the first anchor device within an obturator foramen;
   inserting the second anchor device with the delivery tool through the incision and anchoring the second anchor device within an obturator foramen;
   positioning the tissue support portion of the implant under a urethra; and
   closing the incision.

20. The method of claim 19, wherein inserting the first and second anchor devices further includes unseating the tine ends of the anchor devices from the interior pleat channels prior to anchoring the anchor devices within the obturator foramen.

21. The method of claim 19, wherein a distal region of each of the opposed flared portions is constructed of a generally flexible polymer material.

22. The method of claim 19, wherein a proximal region of each of the opposed flared portions is constructed of a generally rigid polymer material.

* * * * *

UNITED STATES PATENT AND TRADEMARK OFFICE
CERTIFICATE OF CORRECTION

PATENT NO. : 8,678,995 B2  Page 1 of 1
APPLICATION NO. : 13/057186
DATED : March 25, 2014
INVENTOR(S) : Scott Crawford It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 465 days.

Signed and Sealed this
Twenty-ninth Day of September, 2015

Michelle K. Lee
*Director of the United States Patent and Trademark Office*